United States Patent [19]

Bauer et al.

[11] Patent Number: 4,819,633
[45] Date of Patent: Apr. 11, 1989

[54] COAGULATION FORCEPS

[75] Inventors: Siegfried Bauer, Heidelsheim; Ernst Falk, Sternenfels-Diefenbach, both of Fed. Rep. of Germany

[73] Assignee: Richard Wolf GmbH, Fed. Rep. of Germany

[21] Appl. No.: 79,021

[22] Filed: Jul. 29, 1987

[30] Foreign Application Priority Data

Sep. 2, 1986 [DE] Fed. Rep. of Germany ....... 3629809

[51] Int. Cl.[4] .............................................. A61B 17/39
[52] U.S. Cl. ............................................... 128/303.17
[58] Field of Search ........................ 128/303.13–303.17

[56] References Cited

U.S. PATENT DOCUMENTS

| 3,903,892 | 9/1975 | Komiya | 128/303.15 |
| 4,054,143 | 10/1977 | Bauer | 128/303.17 |
| 4,128,099 | 12/1978 | Bauer | 128/303.17 |

FOREIGN PATENT DOCUMENTS

GM7728428  3/1978  Fed. Rep. of Germany .
2156222  10/1985  United Kingdom ........... 128/303.15

Primary Examiner—Lee S. Cohen
Attorney, Agent, or Firm—Hill, Van Santen, Steadman & Simpson

[57] ABSTRACT

The coagulation forceps of the type in which a rod for the opening and closing of forceps jaws by reciprocal axial movement thereof extends axially through an externally insulated shaft, and is actuated by a handle comprising a pair of branches which are resiliently biassed apart from one another. To simplify construction while ensuring that the handle is well insulated from the HF supply to the forceps shaft, the two branches of the handle are connected to respective parts of the forceps by separately produced insulating elements. One of these elements is connected to the proximal end of the actuating rod while the other is mounted on the shaft and encloses a connector for the HF supply.

3 Claims, 1 Drawing Sheet

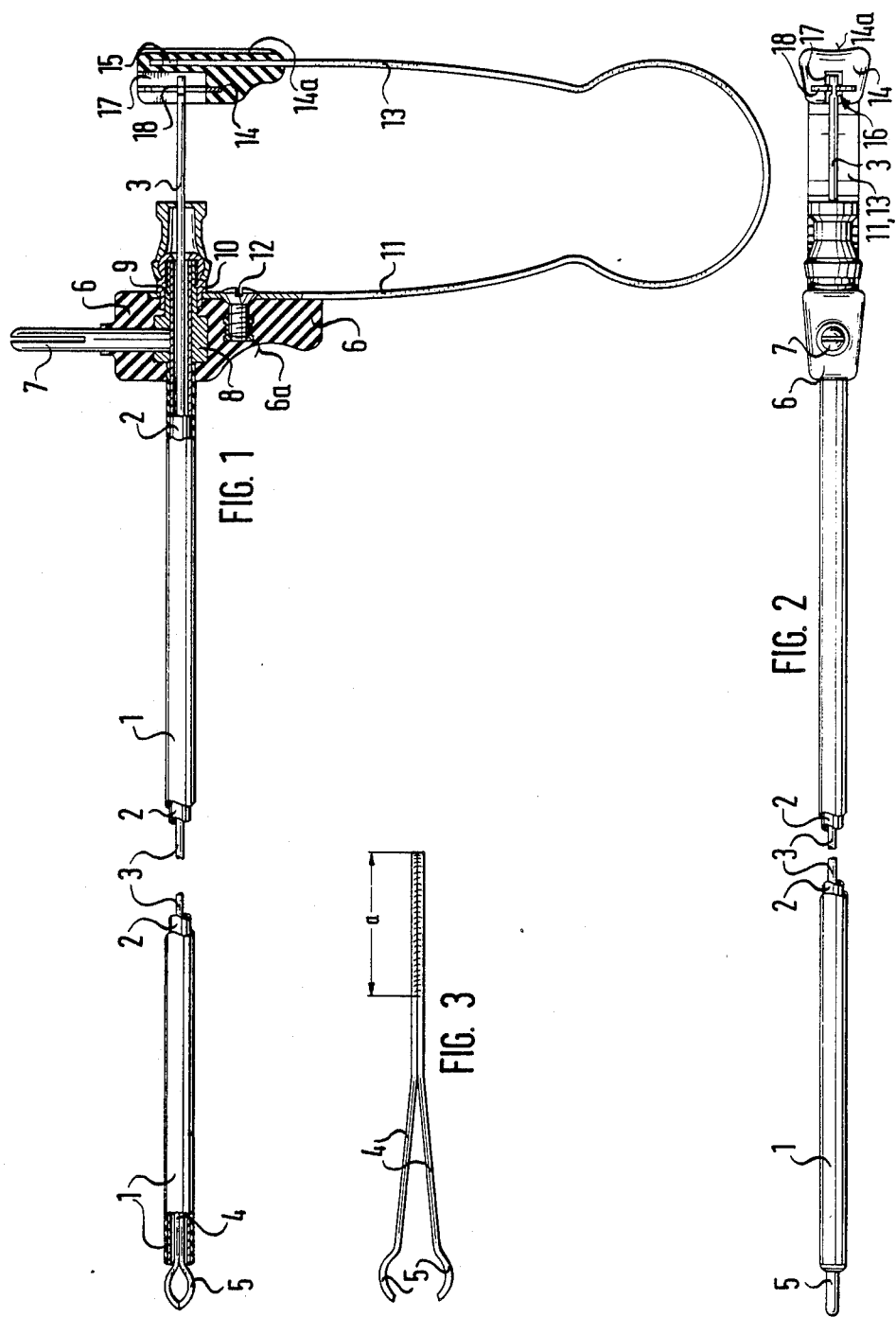

COAGULATION FORCEPS

BACKGROUND TO THE INVENTION

1. Field of the Invention

The invention relates to coagulation forceps in which a metal actuating rod, extending through an externally insulated metal shaft to open and close the forceps jaws is coupled to one branch of a handle having two branches biassed resiliently away from one another, the other branch being connected in an insulated manner to the forceps shaft which is energised by an HF (high frequency) electrical supply.

2. Description of the Prior Art

Coagulation forceps of the aforesaid kind, as described for example in German Utility Model No. 7 728 428, were so constructed in practice that the proximal handle members which were not covered by the shrink-on hose insulating the shaft were encased in an insulating coating of a plastics material, so that a complete insulation was obtained. The plastics material coating could become porous and brittle as a result of protracted use, frequent sterilisation or incorrect handling, which could expose instrument parts and lead to a damaging passage of current.

Coating the forceps elements at the proximal end was also complex and costly, as regards production technology.

SUMMARY OF THE INVENTION

It is an object of the invention to simplify the production and assembly of the insulation of the handle and actuator parts at the proximal end of a monopolar coagulation forceps energised with HF current, and at the same time in preventing the risk of accidental passage of HF current to the patient and the physician.

According to the invention, this object is achieved in that in the case of coagulation forceps of the type referred to in the foregoing, one of the two handle branches is connected via a first insulator element, acting as a thumb stop to the actuating rod and the other handle branch is connected to the forceps shaft via a second insulator element receiving the HF connector, the shaft and the forceps and acting as a stop for the index finger, the insulator elements being as separately produced elements in each case.

According to the invention, the proximal extremity of the shaft and the proximal extremity of the actuating rod of the forceps jaws are coupled to prefabricated insulating elements, which for their part are coupled to the handle branches, so that the production and assembly of the coagulation forceps are substantially simplified thereby, and these insulating elements insulate the proximal metal elements from each other in a particularly problem-free manner, without the occurrence of the risks which arose in the case of the known coating.

Further objects and advantages of the invention will become apparent from the following detailed description when read in conjunction with the accompanying drawings which illustrate a preferred embodiment of the invention.

BRIEF DESCRIPTION OF THE DRAWINGS

FIG. 1 shows a coagulation forceps according to a preferred embodiment of the invention in partial and interrupted longitudinal cross-section, with a partial lateral view of the shaft, FIG. 2 shows a plan view of the forceps according to FIG. 1 and FIG. 3 shows the forceps jaws of FIG. 1 in enlarged lateral elevation.

DETAILED DESCRIPTION OF THE PREFERRED EMBODIMENT

The coagulation forceps shown in the drawings comprise a metal shaft 2, externally encased by a shrink-on hose 1 or by other suitable means insulated through which an actuating rod 3 extends freely to the gripper branches 4 of a pair of jaws 5 of the forceps. The branches 4 and integral jaws 5 of the forceps are produced from resilient metal of semicircular cross-section and the branches are interwelded along a proximal length a and receive the distal extremity of the actuating rod 3.

According to the invention, the proximal shaft extremity is encased in an insulating element 6 of an appropriate plastics material, wherein an HF connector pin 7 is incorporated together with a metal coupling member 8 by an injection casting method during the production of the insulating element 6.

The coupling element 8 is provided with a cylindrical extension 9 projecting in a proximal direction out of the insulating element 6 and provided with an external screwthread, on to which is screwed an insulating tube member 10. The extension 9 is joined by welding to the proximal extremity of the shaft.

The insulating element 6 is provided on its proximal side surface with a shallow recess wherein is placed the upper extremity of one branch 11 of a handle which comprises to branches 11, 13 resiliently biassed apart, the branch 11 being traversed by the extremities of the tubes 8 and 9 and firmly joined to the insulating element 6 by means of a screw 12. The handle is formed integrally from a resilient metal strip bent to form two branches 11,13 with a part-circular connecting portion between them.

The other branch 13 of the spring-loaded handle is provided at its free extremity with an insulating element 14 which is also produced by injection moulding from plastics material, the free upper extremity of the branch 13 being pushed into a recess and retained at 15 by a projection engaging in a recess of the branch 13. The proximal extremity of the actuating rod 3 is connected to this insulating element 14. To this end, the extremity of the rod 3 is provided with a constriction 16 and engages in an incision 17 opening in distal direction, which has two grooves into which may be inserted a slotted disc 18 the slot edges of which engage in the constriction 16 of the rod 3. The disc 18 is again secured in its position by engagement of a projection in a recess of the disc 18. Furthermore, the connection of the handle branch 13 to the actuating rod via the insulating element 14 is such that the forceps jaws 5 are closed by the distal shaft extremity when the two branches 11 and 13 are in the separated, inoperative position towards which they are biassed, as shown in FIG. 1.

As for the rest, the insulating elements 6 and 14 are so shaped that the thumb of a person actuating the forceps is placed against a proximal depression 14a and a pulling finger or index finger engages in a depression 6a or the distal facing side of the insulating element 6, so that the handling action is thereby improved and simplified.

What is claimed is:

1. A coagulation forceps comprising: a tubular metal shaft having an external insulating layer, a distal end and a proximal end, an HF connector being connected to the proximal end of the shaft, a metal actuating rod extending axially through said shaft having a distal end and a proximal end, a pair of forcep jaws being connected to the distal end of said rod to extend out of the distal end of the shaft, actuating means for moving said rod axially in the shaft to move the jaws between a position with the jaws closed to a position with the jaws opened, said actuating means comprising a handle having a first branch and a second branch being urged apart by a spring bias, a first insulator element and a second insulator element being separately produced, said first insulator element being mounted on a free end of the first branch and having means for coupling a proximal end of the rod to said first branch, said second insulator element being mounted on the shaft to surround the proximal end of the shaft and the HF connector and having means forming an insulating connection of the second branch to said shaft, said HF connector being a plug pin having a metal coupling element, said coupling element being provided within the second insulator element and having a cylindrical extension which surrounds the shaft and extends to the proximal end of the shaft, said cylindrical extension having external screw-threads and being welded to the shaft at an extremity of the proximal end of the shaft, an insulating tube cover being threaded on said external screw-threads of the extension, said first insulator element having a recess forming a thumb stop and said second insulator element having a recess forming a stop for a finger so that pressing the insulator elements towards one another with the thumb and finger causes the actuating rod to move the jaws to an open position.

2. A coagulation forceps according to claim 1, wherein said second insulator element has a recess on a proximally facing surface thereof to receive a branch extremity of said second branch of the handle, said branch extremity having a first perforation and a second perforation, said first perforation receiving the proximal end of the shaft and the insulating cover and the second perforation receiving a screw by means of which said branch extremity is secured to said second insulator element.

3. A coagulation forceps comprising: a tubular metal shaft having a external insulating layer, a distal end and a proximal end, an HF connector being connected to the proximal end of the shaft, a metal actuating rod extending axially through said shaft having a distal end and a proximal end, the proximal end of the actuating rod having a constriction adjacent an extremity of the proximal end, a pair of forcep jaws being connected to the distal end of said rod to extend out of the distal end of the shaft, actuating means for moving said rod axially in the shaft to move the jaws between a position with the jaws closed to a position with the jaws opened, said actuating means comprising a handle having a first branch and a second branch being urged apart by a spring bias, a first insulator element and a second insulator element being separately produced, said first insulator element being mounted on a free end of the first branch and having means for coupling a proximal end of the rod to said first branch, said means for coupling including said first insulator element having a recess on a distal side, said recess having two sides with grooves, a disk being received in the grooves in said recess and said disk having a slot receiving the constriction of said rod to couple said rod to the first insulator element, said second insulator element being mounted on the shaft to surround the proximal end of the shaft and the HF connector and having means forming an insulating connection of the second branch to said shaft, said first insulator element having a recess forming a thumb stop and said second insulator element having a recess forming a stop for a finger so that pressing the insulator elements towards one another with the thumb and finger causes the actuating rod to move the jaws to an open position.

* * * * *